US006701921B2

(12) United States Patent
Sprinkel, Jr. et al.

(10) Patent No.: US 6,701,921 B2
(45) Date of Patent: Mar. 9, 2004

(54) AEROSOL GENERATOR HAVING HEATER IN MULTILAYERED COMPOSITE AND METHOD OF USE THEREOF

(75) Inventors: F. Murphy Sprinkel, Jr., Glen Allen, VA (US); Walter A. Nichols, Chesterfield, VA (US); Kenneth A. Cox, Midlothian, VA (US); Timothy S. Sherwood, Midlothian, VA (US); Scott A. Sowers, Richmond, VA (US); Zelita R. Washington, Richmond, VA (US); Sirisha Reddy, Petersburg, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 0 days.

(21) Appl. No.: 09/742,320

(22) Filed: Dec. 22, 2000

(65) Prior Publication Data

US 2002/0078946 A1 Jun. 27, 2002

(51) Int. Cl.[7] .................. A61M 16/00; F23D 11/00; F23D 14/00
(52) U.S. Cl. .................. 128/203.26; 128/203.17; 128/203.27; 128/204.17
(58) Field of Search ............... 128/203.13, 203.15, 128/203.17, 206.26, 203.27, 200.14, 204.17; 261/154, 130, 104, 107; 392/386, 387, 394, 396, 397, 398

(56) References Cited

U.S. PATENT DOCUMENTS

| | | | |
|---|---|---|---|
| 2,896,856 A | 7/1959 | Kravits | |
| 3,084,698 A | 4/1963 | Smith | |
| 3,157,179 A | 11/1964 | Paullus et al. | |

(List continued on next page.)

FOREIGN PATENT DOCUMENTS

| | | |
|---|---|---|
| BE | 354004 A | 9/1928 |
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |

OTHER PUBLICATIONS

Notification of Transmittal of the International Search Report or the Declaration for PCT/US01/45749 dated Oct. 3, 2002.

Barry, P.W. et al. "In Vitro Comparison of the Amount of Salbutamol Available for Inhalation From Different Formulations Used with Different Spacer Devices" Eur Respir J 1997; 10: 1345–1348.

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

(List continued on next page.)

*Primary Examiner*—Weilun Lo
*Assistant Examiner*—Michael G Mendoza
(74) *Attorney, Agent, or Firm*—Burns, Doane, Swecker & Mathis, LLP

(57) ABSTRACT

An aerosol generator includes a fluid passage arranged between a first and a second layer wherein the first and second layers at least partially define the fluid passage. A liquid supply is arranged to provide a fluid in liquid phase to the fluid passage. The aerosol generator also includes a heater arranged to volatilize the fluid in the fluid passage. An outlet of the aerosol generator is arranged to receive the volatilized fluid and direct the volatilized fluid out of the fluid passage. The aerosol generator can be used to generate aerosols containing medicated materials.

30 Claims, 2 Drawing Sheets

U.S. PATENT DOCUMENTS

| | | |
|---|---|---|
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |
| 3,987,941 A | 10/1976 | Blessing |
| 3,993,246 A | 11/1976 | Erb et al. |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,762,995 A | 8/1988 | Browner et al. |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,421,489 A | 6/1995 | Holzner, Sr. et al. |
| 5,462,597 A | 10/1995 | Jubran |
| 5,474,059 A | 12/1995 | Cooper |
| 5,515,842 A | 5/1996 | Ramseyer et al. |
| 5,522,385 A | 6/1996 | Lloyd et al. |
| 5,556,964 A | 9/1996 | Hofstraat et al. |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,617,844 A | 4/1997 | King |
| 5,642,728 A | 7/1997 | Andersson et al. |
| 5,674,860 A | 10/1997 | Carling et al. |
| 5,682,874 A | 11/1997 | Grabenkort et al. |
| 5,730,158 A | 3/1998 | Collins et al. |
| 5,743,250 A * | 4/1998 | Gonda et al. .......... 128/200.14 |
| 5,743,251 A | 4/1998 | Howell et al. |
| 5,756,995 A | 5/1998 | Maswadeh et al. |
| 5,765,724 A | 6/1998 | Amberg et al. |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,869,133 A | 2/1999 | Anthony et al. |
| 5,872,010 A | 2/1999 | Karger et al. |
| 5,878,752 A | 3/1999 | Adams et al. |
| 5,881,714 A | 3/1999 | Yokoi et al. |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,954,979 A | 9/1999 | Counts et al. |
| 5,957,124 A | 9/1999 | Lloyd et al. |
| 5,970,973 A | 10/1999 | Gonda et al. |
| 5,970,974 A | 10/1999 | Van Der Linden et al. |
| 5,978,548 A | 11/1999 | Holmstrand et al. |
| 5,993,633 A | 11/1999 | Smith et al. |
| 6,014,970 A | 1/2000 | Ivri et al. |
| 6,053,176 A | 4/2000 | Adams et al. |
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,076,522 A | 6/2000 | Dwivedi et al. |

| | | |
|---|---|---|
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,196,218 B1 * | 3/2001 | Voges .................... 128/200.14 |
| 6,196,219 B1 * | 3/2001 | Hess et al. ............. 128/200.14 |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 6,325,475 B1 * | 12/2001 | Hayes et al. ........... 128/203.11 |
| 2001/0032647 A1 | 10/2001 | Schuster et al. |

OTHER PUBLICATIONS

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Inerpharm Press, Buffalo Grove, IL 1998 pp 97–102.

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Developement Laboratories Pack, S–221 01 Lund (Sweden), International Journal of Pharmaceutics, 1 (1978) 205–212.

Newman, Stephen P. et al. "Deposition of Pressurized Suspension Aerosols Inhaled Through Extension Device[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Phamaceutical Sciences, vol. 69, No. 7, pp. 766–770, Jul. 1980.

Co–pending application Ser. No. 09/479,597 entitled "Aerosol Generator and Methods of Making and Using an Aerosol Generator" by Kenneth A. Cox et al., filed Jan. 7, 2000.

Co–pending application Ser. No. 09/742,322 entitled "Aerosol Generator Having Multiple Heating Zones and Method of Use Thereof" by Kenneth A. Cox et al., filed Dec. 22, 2000.

Written Opinion for PCT/US01/45759 dated May 28, 2003.

* cited by examiner

AEROSOL GENERATOR HAVING HEATER IN MULTILAYERED COMPOSITE AND METHOD OF USE THEREOF

BACKGROUND OF THE INVENTION

1. Field of the Invention

The present invention relates generally to aerosol generators and, more particularly, to aerosol generators which include a heater in a multilayered composite. The aerosol generators of the invention are able to generate aerosols without requiring the use of compressed gas propellants. The present invention also relates to methods for generating an aerosol. The present invention has particular applicability to the generation of aerosols containing medicated material.

2. Description of the Related Art

Aerosols are gaseous suspensions of fine solid or liquid particles and are useful in a wide variety of applications. For example, medicated liquids and powders may be administered in aerosol form. Such medicated aerosols include, for example, materials which are useful in the treatment of respiratory ailments, in which case the aerosols may be inhaled into a patient's lungs. Aerosols may also be used in non-medicinal applications including, for example, dispensing air fresheners and insecticides and delivering paints and/or lubricants.

In aerosol inhalation applications, it is typically desirable to provide an aerosol having an average mass median particle diameter of less than 2 microns to facilitate deep lung penetration. Most known aerosol generators are incapable of generating aerosols having an average mass median particle diameter less than 2 microns. Also, in certain applications, it is generally desirable to deliver medicated material at high flow rates, for example, above 1 mg per second. Most known aerosol generators suited for delivering medicated material are incapable of delivering material at such high flow rates while maintaining a suitable average mass median particle diameter. In addition, most known aerosol generators deliver an imprecise amount of aerosol compared with the amount of aerosol that is intended to be delivered.

The related art discloses aerosol generators which employ various techniques for delivering an aerosol. A particularly useful technique involves volatilizing a fluid and ejecting the volatilized fluid into the atmosphere. The volatilized fluid subsequently condenses, thereby forming an aerosol. See, for example, commonly assigned U.S. Pat. No. 5,743,251, the entire contents of which document are hereby incorporated by reference. Such aerosol generators may eliminate or conspicuously reduce some or all of the aforementioned problems associated with the known aerosol generators. However, since these aerosol generators employ heat-generating systems, heat resistive material and, in some cases, various control devices, pumps and valves, the manufacture and assembly of such aerosol generators can be complicated and expensive.

In light of the foregoing, there exists a need in the art for the provision of an aerosol which overcomes or conspicuously ameliorates the above described shortcomings in the related art. Accordingly, it is an object of the present invention to provide an aerosol generator having a heater in a multilayered composite, and which produces an aerosol from a fluid by volatilizing the fluid and directing the volatilized fluid therefrom.

It is a further object of the present invention to provide a method for generating an aerosol.

Other objects and aspects of the present invention will become apparent to one of ordinary skill in the art upon review of the specification, drawings and claims appended hereto.

SUMMARY OF THE INVENTION

The foregoing objects are met by the aerosol generators of the present invention. According to a first aspect of the present invention, an aerosol generator is provided. The aerosol generator includes:

(a) a fluid passage arranged between a first layer and a second layer, wherein the first and second layers at least partially define the fluid passage;

(b) a fluid supply arranged to provide a fluid in liquid phase to the fluid passage;

(c) a heater arranged to volatilize the fluid in the fluid passage; and (d) an outlet arranged to receive the volatilized fluid and direct the volatilized fluid out of the fluid passage.

According to another aspect of the present invention, a method for generating an aerosol using an aerosol generator comprising (1) a fluid passage arranged between a first layer and a second layer, wherein the first and second layers at least partially define the fluid passage; (2) a fluid supply arranged to provide a fluid in liquid phase to the fluid passage; (3) a heater arranged to volatilize the fluid in the fluid passage; and (4) an outlet arranged to receive the volatilized fluid and direct the volatilized fluid out of the fluid passage, the method comprising:

(a) heating the heater of the aerosol generator, thereby volatilizing the fluid in the fluid passage; and (b) directing the volatilized fluid out of the fluid passage via the outlet.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Figure 1:
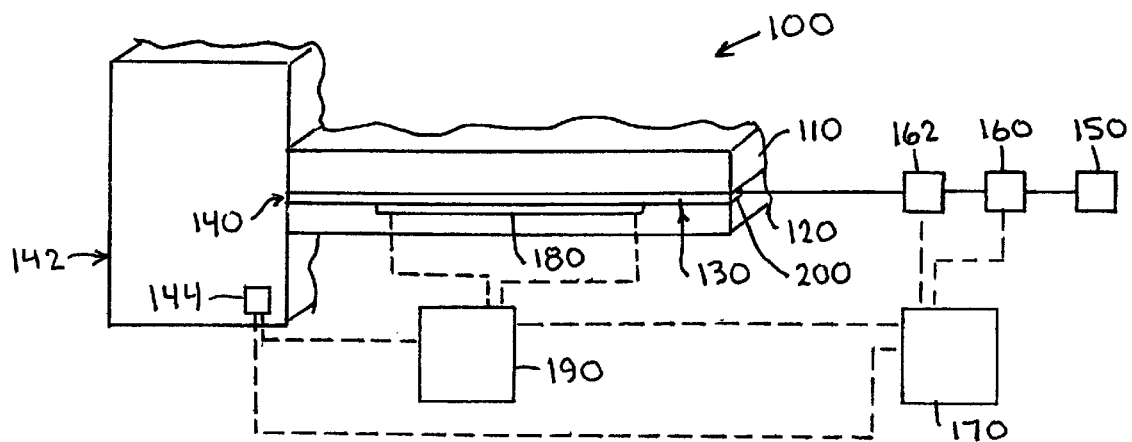
FIGS. 1 and 2 are schematic diagrams of an exemplary aerosol generators in accordance with the invention wherein the generator shown in FIG. 1 includes a single heater and the generator shown in FIG. 2 includes two heaters.

When referring to the drawing figures, like reference numerals designate identical or corresponding elements throughout the several figures.

Figure 2:
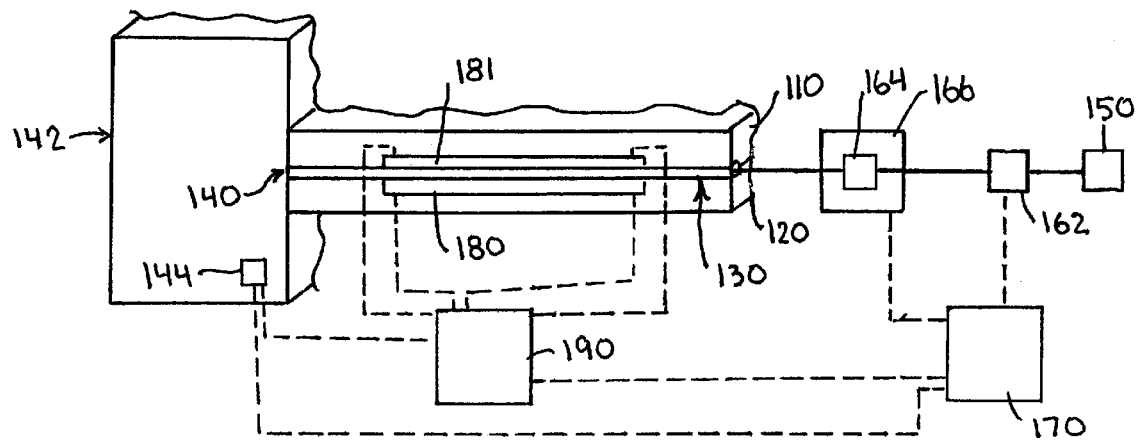

Referring to FIGS. 1 and 2, an aerosol generator 100 according to one aspect of the present invention is shown. The aerosol generator 100 produces an aerosol from a fluid in liquid form by volatilizing the fluid and directing the volatilized fluid away from the aerosol generator 100 and into the atmosphere. The volatilized fluid subsequently condenses, thereby forming an aerosol.

The fluid may include any material capable of volatilization by the aerosol generator 100. In a preferred embodiment, the fluid does not decompose when exposed to the heat required for volatilization thereof. The fluid preferably includes a medicated material such as, for example, a material that is useful in the treatment of respiratory ailments. In such applications, the generated aerosol may be inhaled into a user's lungs. Alternatively, the fluid may include a non-medicated material.

Figure 3:
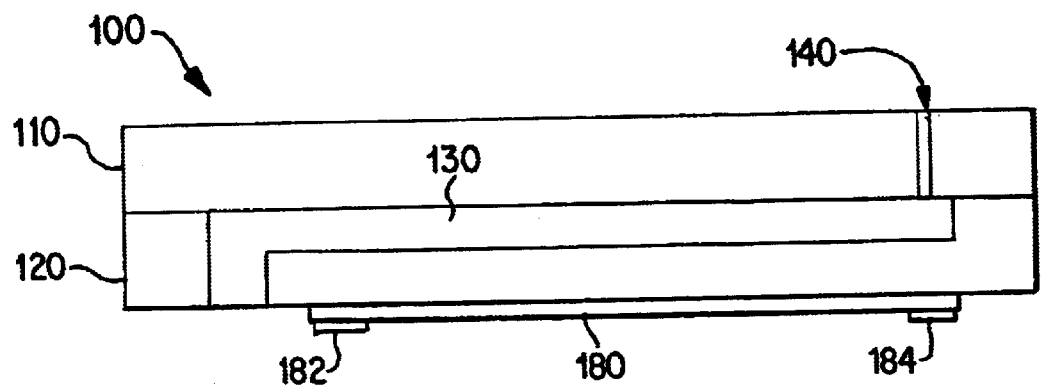
FIG. 3 is an exploded view of an exemplary aerosol generator in accordance with the invention.

Referring to FIGS. 1–3, the aerosol generator 100 includes a fluid passage 130 arranged between a first layer 110 and a second layer 120. The first and second layers 110, 120 are formed from a heat-resistant material that is preferably capable of withstanding the temperatures and pressures generated in the fluid passage 130. The heat-resistant material is more preferably capable of withstanding repeated heating cycles. Also, the heat-resistant material preferably does not react with the fluid contained in the fluid passage 130. The heat-resistant material may include, for example, alumina, zirconia, silica, aluminum silicate, titania, yttria-stabilized zirconia, magnesia or mixtures thereof, preferably alumina. The first and second layers 110, 120 may be of any size suitable for aerosol generation. According to a preferred embodiment, each layer can have a length of from about 1 to 100 mm, more preferably about 15 mm; a width of from about 1 to 100 mm, more preferably about 15 mm; and a thickness of from about 0.001 to 10 mm, more preferably about 0.076 mm.

Figure 4:
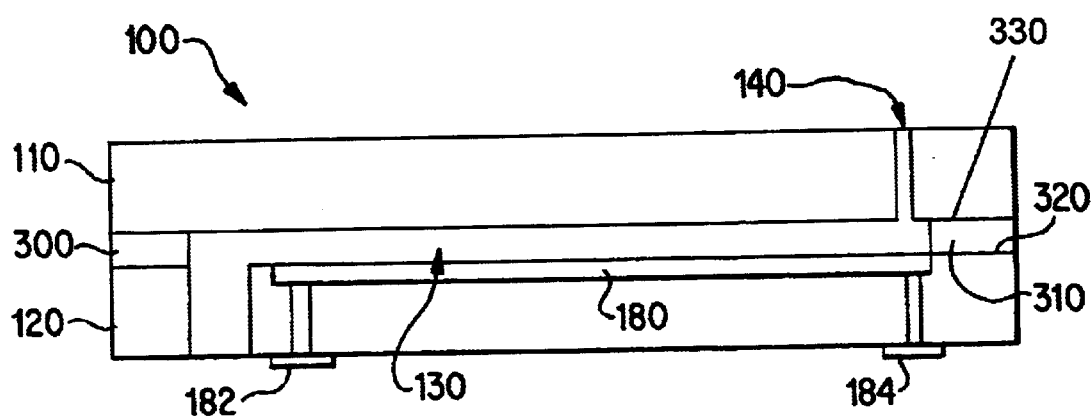
FIG. 4 is an exploded view of an exemplary aerosol generator in accordance with the invention.

The first and second layers 110, 120 at least partially define the fluid passage 130. In the embodiment shown in FIGS. 1 and 3, a channel 200 is formed in a planar surface of the second layer 120. If desired, however, the channel 200 can be formed by adding one or more layers of material between the first and second layers, as shown in FIG. 4. The first and second layers 110, 120 are attached together, thereby enclosing the channel 200 therebetween. In this manner, the channel 200 of the second layer 120 and the first layer 110 define the fluid passage 130. Additionally or alternatively, a further channel may be disposed upon the side of the first layer 110 that is attached to the second layer 120, wherein such additional channel further defines the fluid passage 130, as shown in FIG. 2. The additional channel is preferably arranged such that the additional channel and the channel 200 form a single fluid passage 130 when the first and second layers 110, 120 are attached together.

Referring to FIG. 4, a third layer 300 defining a void space 310 can be arranged between the first and second layers 110, 120. In this case, a first and a second surface 330, 320 of the third layer 300 are attached to the first and second layers 110, 120, respectively, thereby enclosing the third layer 300 therebetween. In this manner, the first and second layers 110, 120 and the void space 310 of the third layer 300 define the fluid passage 130. Further, whereas the embodiments of FIGS. 1 and 2 show a heater arranged inside the flow passage 130, the heater 180 can be located on an outer surface of layer 110, 120 such that heat from the heater is conducted through the layer 110, 120 to volatilize fluid in the flow passage 130.

The aforementioned first, second and third layers 110, 120, 300 may be attached together using various techniques, including, for example, adhesive bonding. The adhesive material used to attach the layers is preferably capable of withstanding repeated heating cycles and may include, for example, a metal, a cement, an epoxy, an acrylic, a cyanoacrylic or mixtures thereof, preferably an acrylic cement. Alternatively, other techniques may be used to attach the layers 110, 120, 300 together such as, for example, mechanical or metallurgical bonding, e.g., use of a brazing material, glass or filled glass to hold the layers together.

The fluid passage 130 is preferably linear to facilitate the flow of the fluid therethrough. Alternatively, the fluid passage 130 can be non-linear such as in the case where the direction of fluid flow through the passage 130 contains at least one turn.

Referring to FIG. 1, the upstream end of the fluid passage 130 is connected to receive a fluid in liquid phase from a fluid supply 150. Volatilized fluid exits the downstream end of the fluid passage 130 through outlet 140. The outlet 140 can be oriented to direct the volatilized fluid in a desired direction and/or the outlet 140 can be sized to achieve a desired aerosol particle size distribution. In a preferred embodiment, the outlet 140 is smaller in size than the channel 200 forming the flow passage 130. For example, the outlet 140 can be a circular opening in an edge of the layer 120 with a diameter of about from 0.002 to 2.5mm, more preferably about 0.2 mm.

According to an exemplary embodiment of the present invention, the outlet 140 is an orifice disposed on the first or second layer 110, 120 through which the volatilized fluid flows. The outlet 140 may be disposed at an angle, for example, 10 to 160°, with respect to the axis of fluid flow within the fluid passage 130, to direct the flow of the volatilized fluid out of the fluid passage 130 in a desired direction. According to an alternative embodiment, the fluid passage 130 extends through a side wall of the layers 110, 120, and the outlet 140 is defined by the furthest downstream portion of the fluid passage 130. A conduit (not shown) may be connected to receive the volatilized fluid from the outlet 140 to further direct the flow of volatilized fluid in a desired direction. Such a conduit preferably has a diameter of from about 0.2 to 50 mm.

In a preferred embodiment, a valve 160 and/or a pump 162 can be used to control the flow of fluid from the liquid supply 150 to the fluid passage 130. The valve 160 and/or the pump 162 may be manually operated. Alternatively, a controller 170 may manipulate the valve 160 and/or the pump 162 based on various parameters including, for example, the amount of time the valve 160 remains in the open position, or the volumetric amount of fluid that is supplied to the fluid passage 130. In this manner, the valve 160 and/or the pump 162 may enable the liquid supply 150 to deliver a predetermined volume of fluid in liquid phase to the fluid passage 130. In an alternative embodiment, the fluid in liquid phase can be contained in a chamber, and a desired amount of the fluid can be delivered to the flow passage 130 by compressing the fluid in the chamber using a piston, e.g., the fluid can be supplied by a syringe pump.

Another mechanism for delivering the fluid is shown in FIG. 2 wherein fluid is supplied, via pump 162 or other suitable arrangement, to a chamber 164 of a device such as a metering valve 166. Exemplary embodiments of such metering valves are described in U.S. patent application Ser. No. 09/479,597 filed on Jan. 7, 2000, the disclosure of which is hereby incorporated by reference. With such an arrangement, the chamber 164 can be filled with a predetermined volume of fluid, preferably an amount sufficient to deliver a single dose of the fluid to the fluid passage 130.

The liquid supply 150 provides the fluid to be volatilized in liquid phase to the fluid passage 130. The fluid in liquid phase may be stored in the liquid supply 150 at a pressure above atmospheric to facilitate delivery of the fluid to the fluid passage 130. In an exemplary embodiment, the liquid supply 150 comprises a refillable storage chamber formed of a material suitable for containing the fluid to be volatilized. Alternatively, the liquid supply 150 comprises a disposable storage chamber which, upon exhaustion of the fluid, is discarded and replaced by a new storage chamber.

The fluid passage 130 may contain any amount of fluid in liquid phase which is capable of being volatilized by the heater 180 of the aerosol generator 100. For example, the fluid passage 130 may have a liquid volumetric capacity of from about $1 \times 10^{-6}$ ml to 0.005 ml. Alternatively, the fluid passage 130 may have a liquid volumetric capacity of greater than about 0.005 ml, preferably from about 0.1 ml to 1.0 ml. In aerosol inhalation applications, the fluid passage 130 may have a liquid volumetric capacity which is sufficient for containing a predetermined amount of fluid that comprises a metered quantity of fluid.

Referring to FIGS. 1–3, the aerosol generator 100 includes a heater 180 which is arranged to volatilize the fluid present in the fluid passage 130. A power supply 190 provides the energy to heat the heater 180. The power supply 190 may include, for example, a battery. In the embodiment shown in FIG. 1, the heater 180 is arranged in direct contact with the fluid contained in the fluid passage 130. In this embodiment, the heater 180 is disposed upon the first and/or second layers 110, 120, for example, inside the channel 200 of the second layer 120. Alternatively, the heater 180 may be disposed upon the first layer 110 such that when the first and second layers 110, 120 are attached together, the heater 180 is arranged inside the fluid passage 130. If desired, more than one heater can be used to volatilize the fluid in the fluid passage 130. For example, multiple heaters can be located along the length of the fluid passage and/or on either side of the fluid passage, e.g., a second heater 181 can be provided on layer 110 in addition to the heater on layer 120, as shown in FIG. 2.

In an alternative embodiment of the present invention, the heater 180 may be coated with a passive layer, such as glass. The coated heater 180 may then be arranged in direct contact with the fluid in the fluid passage 130, as described above.

In a further alternative embodiment of the present invention, the heater 180 may be arranged to conduct heat, through the first and/or second layers 110, 120, to the fluid in the fluid passage 130. In this embodiment, the heater 180 is preferably disposed on the surface of the first and/or second layers 110, 120 which is opposite the surface upon which the fluid passage 130 is disposed, as shown in FIG. 4.

The heater 180 preferably includes a film formed from an electrically resistive heating material which is different from the heat-resistant material used to form the layers 110, 120 of the aerosol generator 100. For example, the resistive material may comprise any resistive heating material such as an electrically conductive ceramic, pure metal, metal alloy or metal compound such as platinum, titanium nitride, stainless steel, nickel chromium, tungsten, molybdenum, or mixtures thereof. Additional resistive materials include composite layers such as self-regulating heater materials. The heater 180 may be sized to be capable of generating a sufficient amount of heat to vaporize the fluid present in the fluid passage 130. In a preferred embodiment, the heater 180 has a length of from about 1 to 100 mm, more preferably about 10 mm; a width of from about 0.1 to 10 mm, more preferably about 0.5 mm; a thickness of from about 1 to 10 microns, more preferably about 3 microns; and an electrical resistance of from about 0.1 to 10 ohms, more preferably about 0.65 ohm.

Using a material for forming the heater 180 which is different from the material used to form the layers 110, 120 allows the resistance through the heater 180 to be easily adjusted by varying various parameters including, for example, the dimensions and the material of the heater 180. In this manner, the resistance of the heater 180 and the amount of heat produced by the heater 180 may be adjusted for various applications.

The resistive material of the heater 180 may be attached to the first and/or second layers 110, 120 using various techniques. For example, the resistive material may be sputtered, printed, bonded or coated upon the first and/or second layers 110, 120. Deposition by sputtering includes, for example, DC magnetron or RF sputter deposition. Deposition by bonding includes, for example, eutectically bonding the resistive material. Printed material can include, for example, screen printed pastes of platinum, silver, gold, tantalum, tungsten, iron and its alloys, and/or alloys containing aluminum. Alternatively, vacuum evaporation, chemical deposition, electroplating and chemical vapor deposition may be used to deposit the resistive material. Contacts and conductive pathways from the heater element to the power source can be made of gold, copper, silver, aluminum or other suitable material. For example, vias extending to the heater 180, 181 can be formed in layer 110 and/or layer 120 and the vias can be filled with conductive material to form the contacts.

Various factors contribute to the stability of the bond between the heater 180 and the first and/or second layers 110, 120. For example, to enhance bonding, the arithmetic average of the surface roughness of the surface upon which the resistive material is disposed preferably is greater than or equal to about 1 microinch, more preferably from about 1 to 100 microinches, and most preferably from about 12 to 22 microinches. In addition, the heat-resistant material of the first and/or second layers 110, 120 and the resistive material of the heater 180 preferably have comparable coefficients of thermal expansion to minimize or prevent thermally induced delamination. The preferred heater material is a 0.1 to 5$\mu$m thick layer of platinum.

In a preferred embodiment, the heater 180 is in electrical contact with first and second contacts 182, 184 (as shown in FIG. 4) which pass an electrical current through the heater 180. In this embodiment, the power supply 190 which provides the electrical current to the heater 180 is in electrical contact with the first and second contacts 182, 184.

The first and second contacts 182, 184 of the heater 180 are preferably formed from a material which has a lower resistance than that of the resistive material of the heater 180. For example, the first and second contacts 182, 184 typically include copper or a copper alloy such as, for example, phosphor bronze and Si bronze, and preferably copper or a copper alloy comprising at least 80% copper or a laminate of gold and silver on copper. Use of such materials prevents or reduces the heating of the contacts 182, 184 prior to the heating of the heater 180. The contacts 182, 184 are sized to be capable of passing an electrical current through the heater 180. The contacts 182, 184 may be attached to the layers 110, 120 and/or heater 180 using any of the techniques used to attach the resistive material to the layers 110, 120, as discussed above.

In each of the above embodiments, a single heater or multiple heaters may be used. The use of multiple heaters in the aerosol generator 100 may enable a more uniform distribution of heat within the fluid passage 130. Alternatively, the use of multiple heaters may enable different zones of the fluid passage 130 to be maintained at different temperatures. Such differing temperature zones in the fluid passage 130 may be useful in fluid temperature control devices, as discussed in U.S. application Ser. No.

09/742,322, filed on Dec. 22, 2000, the entire contents of which document are incorporated by reference herein.

The aerosol generator 100 may generate an aerosol either on an intermittent or continuous basis. For intermittent generation of an aerosol, for example, the fluid supply 150 provides the fluid in liquid phase to the fluid passage 130 each time the generation of an aerosol is desired. The valve 160 and/or the pump 162 may be used to actuate the flow of fluid from the liquid supply 150 to the fluid passage 130. The remaining fluid in liquid phase between the liquid supply 150 and the fluid passage 130 is prevented from traveling back into the liquid supply 150 by any suitable device such as the valve 160 and/or the pump 162 to prevent expansion of the volatilized fluid in the direction opposite the outlet 140.

For generating an intermittent aerosol in inhalation applications, the aerosol generator 100 is preferably provided with a puff-actuated sensor 144, which is preferably arranged inside a mouthpiece 142 disposed proximate to the outlet 140. The puff-actuated sensor 144 can be used to actuate the valve 160 and/or the pump 162 and the heater 180 so that the fluid supply 150 provides the fluid in liquid phase to the fluid passage 130, and the fluid is volatilized by the heater 180. The puff-actuated sensor 144 is preferably sensitive to pressure drops occurring in the mouthpiece 142 when a user draws on the mouthpiece 142. The aerosol generator 100 is preferably provided with circuitry such that, when a user draws on the mouthpiece 142, the valve 160 and/or pump 162 supply fluid in liquid phase to the fluid passage 130 and the heater 180 is heated by the power supply 190.

A puff-actuated sensor 144 suitable for use in the aerosol generator 100 includes, for example, Model 163PC01D35 silicon sensor, manufactured by the MicroSwitch division of Honeywell, Inc., located in Freeport, Ill., or SLP004D 0-4" $H_2O$ Basic Sensor Element, manufactured by SenSym, Inc., located in Milpitas, Calif. Other known flow-sensing devices, such as those using hot-wire anemometry principles, may also be suitable for use with the aerosol generator 100.

In order to further illustrate the present invention and the advantages thereof, the following specific example is given which is intended to be illustrative and in no way limiting.

EXAMPLE

An aerosol generator includes first and second alumina layers each having a length of 15 mm, a width of 15 mm, and a thickness of 0.076 mm. A platinum film is deposited proximate to the center of the first alumina layer. The platinum film has a length of 10 mm, a width of 0.5 mm, and a thickness of 3 microns. Copper contacts are arranged at each end of the platinum film. Acrylic cement is used to bond the second alumina layer to the side of the first alumina layer bearing the platinum film. A cavity is disposed in the second alumina layer proximate the center thereof, on the side of the second layer that is bonded to the first layer. The cavity has a length of 10 mm, a width of 0.5 mm, and a depth of 0.05 mm. The cavity is arranged such that when the first and second alumina layers are bonded together, the platinum film is located inside the cavity. First and second apertures are disposed through the second layer, each aperture being in fluid communication with the cavity. The first aperture is connected to receive fluid from a fluid supply and the second aperture has a diameter of 0.1 mm. Liquid supplied to the first aperture fills the cavity and is volatilized by passing current through the platinum film. As a result, an aerosol is produced by the volatilized fluid exiting the second aperture.

While the invention has been described in detail with reference to preferred embodiments thereof, it will be apparent to one skilled in the art that various changes can be made, and equivalents employed, without departing from the scope of the invention.

What is claimed is:

1. An aerosol generator, comprising:
    (a) a fluid passage arranged between a first and a second layer, wherein the first and second layers at least partially define the fluid passage;
    (b) a fluid supply arranged to provide a fluid in liquid phase to the fluid passage;
    (c) a heater arranged to volatilize the fluid in the fluid passage; and
    (d) an outlet arranged to receive the volatilized fluid and direct the volatilized fluid out of the fluid passage, the outlet having a diameter of from 0.1–0.5 mm.

2. The aerosol generator of claim 1, wherein the fluid passage comprises a channel disposed in the first and/or second layers.

3. The aerosol generator of claim 1, wherein the first layer is bonded to the second layer by a material selected from the group consisting of a glass, metal, a cement, an epoxy, an acrylic, a cyanoacrylic and mixtures thereof.

4. The aerosol generator of claim 1, wherein the first layer is mechanically attached to the second layer.

5. The aerosol generator of claim 1, wherein the first layer comprises a material selected from the group consisting of alumina, zirconia, silica and mixtures thereof.

6. The aerosol generator of claim 1, wherein the second layer comprises a material selected from the group consisting of alumina, zirconia, silica and mixtures thereof.

7. The aerosol generator of claim 1, wherein the heater is arranged to directly contact the fluid in the fluid passage.

8. The aerosol generator of claim 1, wherein the heater is arranged to conduct heat, through the first and/or second layer, to the fluid in the fluid passage.

9. The aerosol generator of claim 1, wherein the heater comprises a material selected from the group consisting of platinum, titanium nitride, stainless steel, nickel chromium, aluminum or alloy thereof, iron or alloy thereof, iron or titanium aluminide, titanium or alloy thereof, tungsten or alloy thereof, and mixtures thereof.

10. The aerosol generator of claim 1, further comprising a second heater, wherein the heater is disposed upon the first layer and the second heater is disposed upon the second layer.

11. The aerosol generator of claim 1, wherein the heater is sputtered, printed, adhesively bonded or coated on the first and/or second layer.

12. The aerosol generator of claim 1, wherein the fluid passage is a linear passage.

13. The aerosol generator of claim 1, wherein the fluid passage is a non-linear passage, a tapered passage, and/or a segmented passage wherein the flow passage has different sized cross sections.

14. The aerosol generator of claim 1, wherein the heater is in electrical contact with first and second contacts which pass an electrical current through the heater, and wherein the volatilized fluid is ejected from the fluid passage when the electrical current is passed through the heater.

15. The aerosol generator of claim 14, wherein the first and second contacts comprise copper or alloy thereof, gold or alloy thereof, or silver or alloy thereof.

16. The aerosol generator of claim 1, wherein the fluid comprises a medicated material.

17. The aerosol generator of claim 1, further comprising a power supply for heating the heater.

18. The aerosol generator according to claim 1, wherein the fluid passage contains from about 0.000001 ml to 0.005 ml of fluid.

19. The aerosol generator according to claim 1, wherein the outlet extends through a surface of the first or second layer.

20. The aerosol generator according to claim 1, further comprising a chamber connected to receive the fluid in liquid phase from the fluid supply and to provide the fluid to the fluid passage, wherein the chamber contains a predetermined amount of the fluid in liquid phase.

21. The aerosol generator according to claim 1, wherein the heater comprises a uniformly thick layer of resistance heating material having a rectangular or tapered shape, a uniformly thick layer of resistance heating material having a plurality of discrete segments, a layer of resistance heating material which varies in thickness, or a layer of resistance heating material which varies in width.

22. An aerosol generator, comprising:
 (a) a fluid passage arranged between a first and a second layer, the first and second layers at least partially defining the fluid passage;
 (b) a third layer defining a void space, the third layer being arranged between the first and second layers, and the fluid passage being further defined by the third layer defining the void space;
 (c) a fluid supply arranged to provide a fluid in liquid phase to the fluid passage;
 (d) a heater arranged to volatilize the fluid in the fluid passage; and
 (e) an outlet arranged to receive the volatilized fluid and direct the volatilized fluid out of the fluid passage.

23. The aerosol generator of claim 22, wherein a first surface of the third layer is bonded to the first layer, and/or a second surface of the third layer is bonded to the second layer, by a material selected from the group consisting of a glass, a metal, a cement, an epoxy, an acrylic, a cyanoacrylic and mixtures thereof.

24. The aerosol generator of claim 22, wherein a first surface of the third layer is mechanically attached to the first layer and/or a second surface of the third layer is mechanically attached to the second layer.

25. The aerosol generator of claim 22, wherein the third layer comprises a material selected from the group consisting of alumina, zirconia, silica and mixtures thereof.

26. A method for generating an aerosol, comprising the steps of:
 (a) supplying fluid to a fluid passage arranged between a first and a second layer, wherein the first and second layers at least partially define the fluid passage and a heater is arranged to volatilize the fluid in the fluid passage and supply the volatilized fluid to an outlet which directs the volatilized fluid out of the fluid passage, the outlet having a diameter of from 0.1–0.5 mm;
 (b) heating the heater so as to volatilize the fluid in the fluid passage; and
 (c) directing the volatilized fluid out of the fluid passage via the outlet.

27. The method of claim 26, wherein the heater heats the fluid in the fluid passage by thermal conduction.

28. The method of claim 26, wherein the heater heats the fluid by thermal conduction through the first and/or second layer.

29. The method of claim 26, wherein the fluid passage comprises a channel disposed in the first and/or second layers and the volatilized fluid is ejected through an opening in a surface of the first and/or second layers.

30. An aerosol generator, comprising:
 a fluid passage between a first layer and a second layer, the first layer and the second layer at least partially defining the fluid passage;
 a fluid supply disposed to provide a metered quantity of a fluid in liquid phase to the fluid passage;
 a heater disposed to volatilize the metered quantity of the fluid in the fluid passage; and
 an outlet disposed to receive the volatilized fluid and direct the volatilized fluid out the fluid passage.

* * * * *